(12) United States Patent
Ishigaki et al.

(10) Patent No.: US 11,983,801 B2
(45) Date of Patent: May 14, 2024

(54) DISPLAY CONTROL APPARATUS, DISPLAY CONTROL METHOD, AND DISPLAY CONTROL PROGRAM

(71) Applicant: FUJIFILM Corporation, Tokyo (JP)

(72) Inventors: Junichi Ishigaki, Tokyo (JP); Eiichi Imamichi, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 17/819,358

(22) Filed: Aug. 12, 2022

(65) Prior Publication Data

US 2022/0392124 A1 Dec. 8, 2022

Related U.S. Application Data

(63) Continuation of application No. PCT/JP2020/036595, filed on Sep. 28, 2020.

(30) Foreign Application Priority Data

Mar. 9, 2020 (JP) .................................. 2020-040359

(51) Int. Cl.
*G06T 11/20* (2006.01)
*G06F 3/04855* (2022.01)
*G06T 11/00* (2006.01)

(52) U.S. Cl.
CPC ........ *G06T 11/203* (2013.01); *G06F 3/04855* (2013.01); *G06T 11/001* (2013.01); *G06T 2200/24* (2013.01)

(58) Field of Classification Search
None
See application file for complete search history.

(56) References Cited

U.S. PATENT DOCUMENTS

2009/0279753 A1    11/2009   Sakaida
2010/0141654 A1    6/2010   Neemuchwala et al.
(Continued)

FOREIGN PATENT DOCUMENTS

JP    2004-173910 A    6/2004
JP    2008-006187 A    1/2008
(Continued)

OTHER PUBLICATIONS

International Search Report issued in PCT/JP2020/036595; dated Oct. 27, 2020.
(Continued)

*Primary Examiner* — Nicholas J Lee
(74) *Attorney, Agent, or Firm* — Studebaker & Brackett PC

(57) ABSTRACT

A display control apparatus performs control to display a designation object for designating a tomographic position corresponding to each of a plurality of tomographic images, and a tomographic image corresponding to a designated tomographic position. For a tomographic image with additional information that includes user-added additional information and computer-added additional information and that is set to be added on a tomographic-image by tomographic-image basis, the display control apparatus performs control to display a marking representing the additional information at a position corresponding to a tomographic position of the tomographic image with the additional information on the designation object. If the additional information is added to the tomographic image corresponding to the designated tomographic position, the display control apparatus performs control to display the marking representing the additional information in an emphasized manner.

14 Claims, 14 Drawing Sheets

(56) References Cited

U.S. PATENT DOCUMENTS

2015/0279061 A1 10/2015 Kutsuna et al.
2016/0120495 A1 5/2016 Miyazawa
2020/0121393 A1* 4/2020 Nakamura ............ G06T 19/003

FOREIGN PATENT DOCUMENTS

| JP | 2015-198928 A | 11/2015 |
| JP | 6419441 B2 | 11/2018 |
| WO | 2014/203940 A1 | 12/2014 |

OTHER PUBLICATIONS

Written Opinion of the International Searching Authority issued in PCT/JP2020/036595; dated Oct. 27, 2020.
An Office Action; "Notice of Reasons for Refusal," mailed by the Japanese Patent Office dated Aug. 29, 2023, which Corresponds to Japanese Patent Application No. 2022-505744 and is related to U.S. Appl. No. 17/819,358; with English language translation.
An Office Action; "Notice of Reasons for Refusal," mailed by the Japanese Patent Office on Jan. 9, 2024, which corresponds to Japanese Patent Application No. 2022-505744 and is related to U.S. Appl. No. 17/819,358; with English language translation.

* cited by examiner

FIG. 11
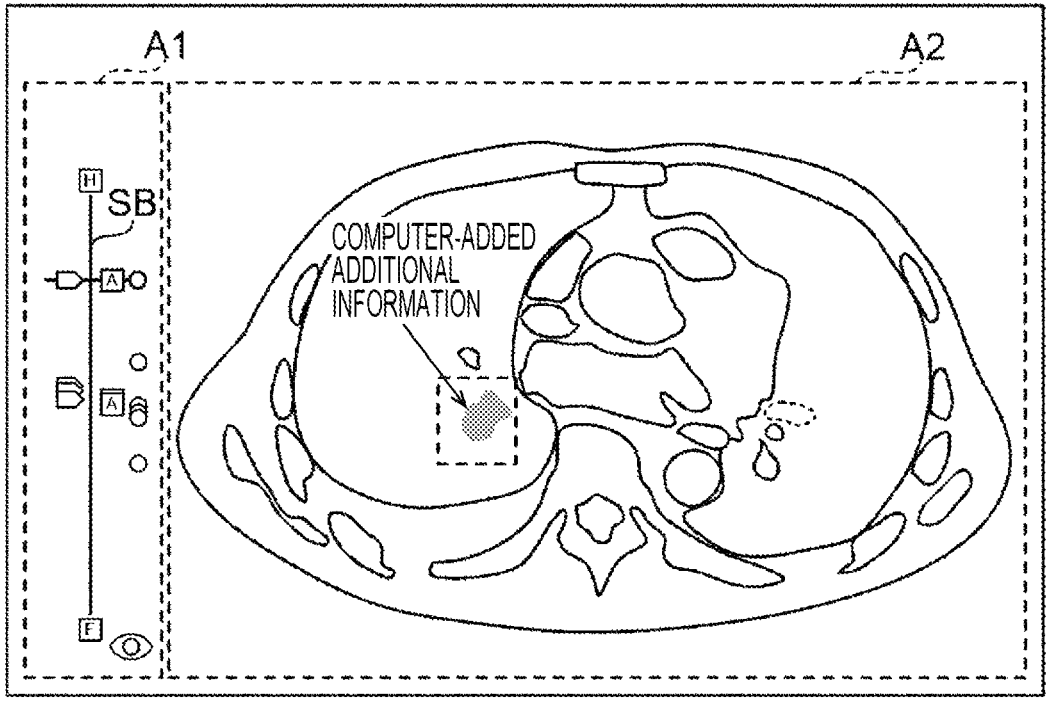
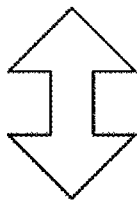
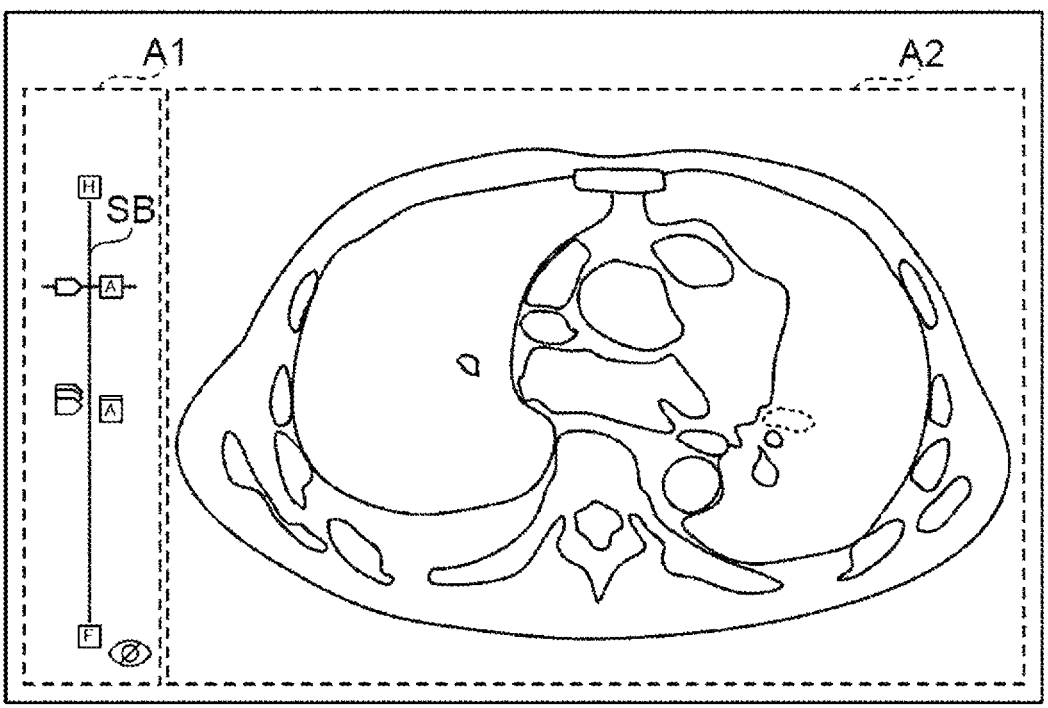

DISPLAY CONTROL APPARATUS, DISPLAY CONTROL METHOD, AND DISPLAY CONTROL PROGRAM

CROSS-REFERENCE TO RELATED APPLICATION

This application is a continuation application of International Application No. PCT/JP2020/036595 filed Sep. 28, 2020, the disclosure of which is incorporated herein by reference in its entirety. Further, this application claims priority from Japanese Patent Application No. 2020-040359 filed on Mar. 9, 2020, the disclosures of which is incorporated herein by reference in its entirety.

BACKGROUND

1. Technical Field

The present disclosure relates to a display control apparatus, a display control method, and a display control program.

2. Description of the Related Art

In recent years, image-based diagnosis has been performed using a three-dimensional medical image captured with imaging apparatuses such as a computed tomography (CT) apparatus and a magnetic resonance imaging (MRI) apparatus. Such a three-dimensional image includes tomographic images at a plurality of tomographic positions different from each other. In image-based diagnosis performed by a doctor using the three-dimensional image, the plurality of tomographic images are switched between and displayed.

A technique for displaying a slider bar for designating a tomographic position corresponding to each of a plurality of tomographic images has been proposed (see JP2004-173910A) as a technique for switching between and displaying the plurality of tomographic images. In this technique, a slider is displayed on the slider bar. A user moves the slider to designate a tomographic position. Then, a tomographic image corresponding to the designated tomographic position is displayed. In this technique, for example, at a tomographic position corresponding to a tomographic image that includes a result (hereinafter, referred to as a "computer diagnosis result") of image-based diagnosis performed by a computer such as an abnormal shadow candidate, a marking indicating inclusion of the computer diagnosis result is also displayed beside the slider bar.

A technique for displaying a label indicating a name of an organ included in a tomographic image corresponding to a tomographic position designated by a slider bar has also been proposed (see JP6419441B).

SUMMARY

In the technique described in JP2004-173910A, a user may have difficulty in grasping whether or not additional information such as a computer diagnosis result is added to a tomographic image at a designated tomographic position if a marking is simply displayed beside the slider bar. The user may have difficulty in grasping whether or not the additional information is added to a tomographic image at a tomographic position designated by the user using the slider or whether or not the additional information is added to an adjacent tomographic image particularly when the number of tomographic images is large. The reason for this is that when the number of tomographic images is large and the additional information is added to each of a plurality of tomographic images at adjacent tomographic positions, a plurality of markings each corresponding to the additional information overlap as a result of concentration of the plurality of markings beside the slider bar. The additional information such as the computer diagnosis result described in JP2004-173910A is additional information unique to each tomographic image because the additional information added to each tomographic image and a marking corresponding to the additional information are associated with each other on a one-to-one basis. As described above, in the technique described in JP2004-173910A, the user may have difficulty in grasping whether or not unique additional information is added to a tomographic image corresponding to a tomographic position designated on the slider bar.

The technique described in JP6419441B is merely a technique for displaying a label of a name of an organ included in a tomographic image corresponding to a designated tomographic position. Thus, in the technique described in JP6419441B as in JP2004-173910A, the user may have difficulty in grasping whether or not unique additional information is added to a tomographic image corresponding to a tomographic position designated on the slider bar.

The additional information added to a tomographic image described in JP6419441B is additional information added to an organ and thus is not additional information unique to each tomographic image for which the additional information added to each tomographic image is associated with a label on a one-to-one basis. For example, even if designation of the tomographic position is changed on the slider bar, the additional information added to each tomographic image is the same as long as tomographic images at tomographic positions before and after the change contain the same organ. Thus, the label of the name of the same organ is displayed. This indicates that one label is associated with a plurality of pieces of additional information added to a plurality of tomographic images including the same organ. Thus, as described above, in the technique described in JP6419441B as in JP2004-173910A, the user may have difficulty in grasping whether or not unique additional information is added to a tomographic image corresponding to a tomographic position designated on the slider bar.

The present disclosure is made in view of the circumstances described above, and an object thereof is to provide a display control apparatus, a display control method, and a display control program that make it easier for a user to grasp whether or not unique additional information is added to a tomographic image corresponding to a tomographic position designated by a designation object.

A display control apparatus according to the present disclosure is a display control apparatus including at least one processor. The processor performs control to display a designation object for designating a tomographic position corresponding to each of a plurality of tomographic images for medical use obtained through imaging of a subject, and a tomographic image corresponding to a designated tomographic position; control to display, for a tomographic image with additional information that is set to be added on a tomographic-image by tomographic-image basis, a marking representing the additional information at a position corresponding to a tomographic position of the tomographic image with the additional information in a depth direction of the designation object, the additional information including at least one of user-added additional information added by a user or computer-added additional information added by a computer and being unique to each of the plurality of tomographic images, the marking being a single marking configured to enable a single tomographic image to be identified; and control to display, in a case where the additional information is added to the tomographic image corresponding to the designated tomographic position, the marking representing the additional information in an emphasized manner. The depth direction refers to a depth direction of the plurality of tomographic images.

In the display control apparatus according to the present disclosure, the designation object may include a slider bar.

In the display control apparatus according to the present disclosure, the designation object may include a schema.

In the display control apparatus according to the present disclosure, the processor may perform control to display the slider bar such that a color of a portion from an end of the slider bar to the designated tomographic position and a color of a portion from an other end of the slider bar to the designated tomographic position are different from each other.

In the display control apparatus according to the present disclosure, the additional information may include the computer-added additional information, and the processor may perform control to display a marking representing the computer-added additional information added to a yet-to-be-displayed tomographic image and a marking representing the computer-added additional information added to an already-displayed tomographic image to be distinguishable from each other.

In the display control apparatus according to the present disclosure, the additional information may include the computer-added additional information, and the processor may receive an input indicating whether or not the computer-added additional information is correct, and perform control to change a color of the marking representing the computer-added additional information from a current display color to a color closer to a background color in a case of receiving an input indicating that the computer-added additional information is incorrect.

In the display control apparatus according to the present disclosure, the additional information may include the computer-added additional information, and the processor may receive an input for switching between displaying and hiding of the computer-added additional information, and perform control to switch between displaying and hiding of the marking representing the computer-added additional information in accordance with the received input.

In the display control apparatus according to the present disclosure, the processor may perform control to display, for a tomographic image with the computer-added additional information, the computer-added additional information over the tomographic image, and perform control to switch between displaying and hiding of both the marking representing the computer-added additional information and the computer-added additional information over the tomographic image in accordance with the received input.

In the display control apparatus according to the present disclosure, the additional information may include, as the computer-added additional information, an outline of a region of interest in the tomographic image, and the processor may perform control to display, in a case where the outline of the region of interest is added to the tomographic image corresponding to the designated tomographic position, the outline of the region of interest over the tomographic image, and perform control to further display an outline of the region of interest added to any of other tomographic images in which a region of interest identical to the region of interest being displayed is detected.

In the display control apparatus according to the present disclosure, the processor may perform control to display a largest outline among outlines of the region of interest added to the other tomographic images.

In the display control apparatus according to the present disclosure, the computer may extract a group of tomographic images containing an identical target from the plurality of tomographic images, and select a representative tomographic image from the extracted group of tomographic images, and the computer-added additional information may include information to be added to the selected tomographic image.

In the display control apparatus according to the present disclosure, the user-added additional information may include information added by the user to a representative tomographic image of a group of tomographic images containing an identical target among the plurality of tomographic images.

A display control method according to the present disclosure is a display control method in which a processor, which a display control apparatus comprises, performs a process of performing control to display a designation object for designating a tomographic position corresponding to each of a plurality of tomographic images for medical use obtained through imaging of a subject, and a tomographic image corresponding to a designated tomographic position; control to display, for a tomographic image with additional information that is set to be added on a tomographic-image by tomographic-image basis, a marking representing the additional information at a position corresponding to a tomographic position of the tomographic image with the additional information in a depth direction of the designation object, the additional information including at least one of user-added additional information added by a user or computer-added additional information added by a computer and being unique to each of the plurality of tomographic images, the marking being a single marking configured to enable a single tomographic image to be identified; and control to display, in a case where the additional information is added to the tomographic image corresponding to the designated tomographic position, the marking representing the additional information in an emphasized manner.

A display control program according to the present disclosure is a display control program for causing a processor, which a display control apparatus comprises, to perform a process of performing control to display a designation object for designating a tomographic position corresponding to each of a plurality of tomographic images for medical use obtained through imaging of a subject, and a tomographic image corresponding to a designated tomographic position; control to display, for a tomographic image with additional information that is set to be added on a tomographic-image by tomographic-image basis, a marking representing the additional information at a position corresponding to a tomographic position of the tomographic image with the additional information in a depth direction of the designation object, the additional information including at least one of user-added additional information added by a user or computer-added additional information added by a computer and being unique to each of the plurality of tomographic images, the marking being a single marking configured to enable a single tomographic image to be identified; and control to display, in a case where the additional information is added to the tomographic image corresponding to the designated tomographic position, the marking representing the additional information in an emphasized manner.

The present disclosure makes it easier for a user to grasp whether or not unique additional information is added to a tomographic image corresponding to a tomographic position designated by a designation object.

BRIEF DESCRIPTION OF THE DRAWINGS

FIG. 11 is a diagram for describing switching between displaying and hiding of the computer-added additional information over a tomographic image;

DETAILED DESCRIPTION

An embodiment for implementing a technique of the present disclosure will be described in detail below with reference to the drawings.

Figure 1:
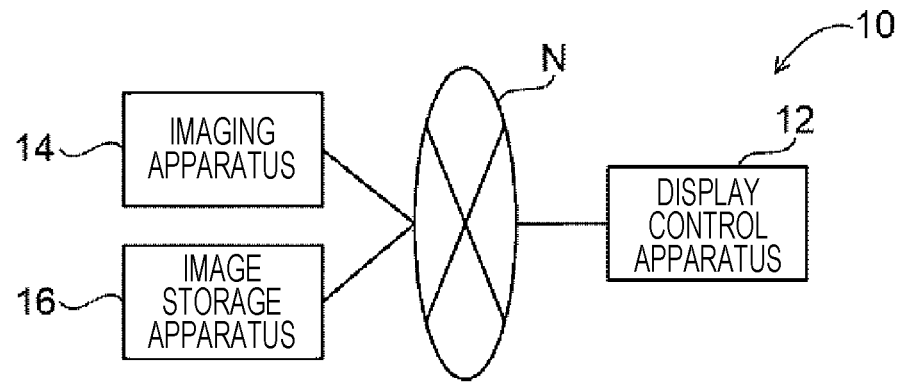
FIG. 1 is a block diagram illustrating an example of a configuration of a diagnosis assistance system.

First, a configuration of a diagnosis assistance system 10 according to the present embodiment will be described with reference to FIG. 1. As illustrated in FIG. 1, the diagnosis assistance system 10 includes a display control apparatus 12, an imaging apparatus 14, and an image storage apparatus 16. The display control apparatus 12, the imaging apparatus 14, and the image storage apparatus 16 are connected to a network N and can communicate with each other via the network N.

The imaging apparatus 14 is an apparatus that images a diagnosis-target part of a subject to generate a three-dimensional medical image representing the part. The three-dimensional medical image captured by the imaging apparatus 14 includes a plurality of tomographic images. In the present embodiment, an example will be described in which a CT apparatus is used as the imaging apparatus 14. However, the imaging apparatus 14 is not limited to this. For example, an apparatus that generates a three-dimensional medical image other than a CT apparatus, such as an MRI apparatus or a positron emission tomography (PET) apparatus, may be used as the imaging apparatus 14. In the present embodiment, an example will be described in which tomographic images of axial cross-sections are used as the tomographic images constituting the three-dimensional medical image. However, the tomographic images are not limited to these. As the tomographic images constituting the three-dimensional medical image, tomographic images of cross-sections other than the axial cross-sections, such as sagittal cross-sections and coronal cross-sections, may be used.

The image storage apparatus 16 is a computer that stores and manages a medical image, and includes a storage device or the like in which the medical image is stored. The image storage apparatus 16 transmits and receives a medical image generated by the imaging apparatus 14 to and from the display control apparatus 12 and the imaging apparatus 14, respectively, via the network N. A storage format of the medical image and communication performed between the apparatuses via the network N are based on a predetermined protocol such as Digital Imaging and Communication in Medicine (DICOM).

A hardware configuration of the display control apparatus 12 according to the present embodiment will be described next with reference to FIG. 2. Examples of the display control apparatus 12 include a personal computer, a server computer, or the like. The display control apparatus 12 may be a cloud server.

Figure 2:
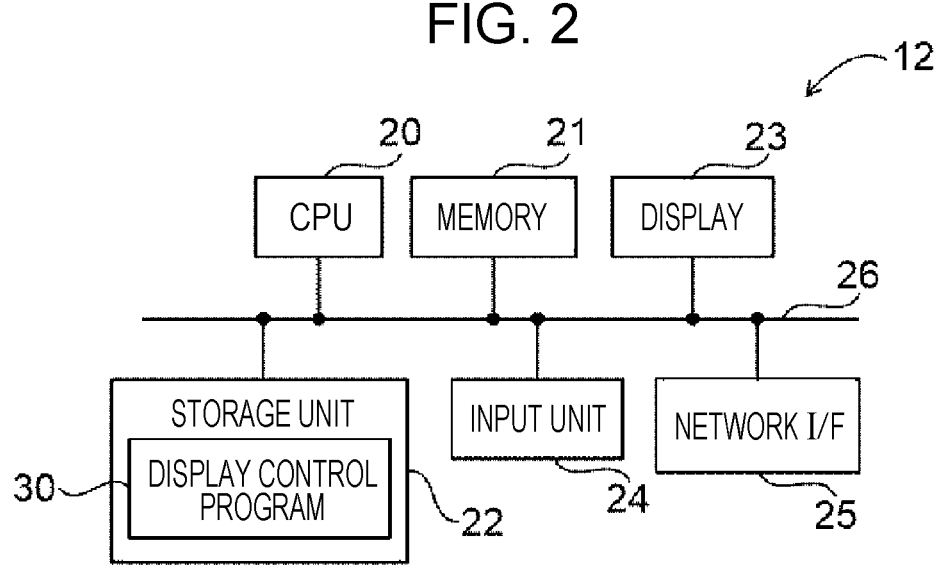
FIG. 2 is a block diagram illustrating an example of a hardware configuration of a display control apparatus.

As illustrated in FIG. 2, the display control apparatus 12 includes a central processing unit (CPU) 20, a memory 21 serving as a temporary storage area, and a storage unit 22 that is nonvolatile. The display control apparatus 12 also includes a display 23 such as a liquid crystal display, an input unit 24 such as a keyboard and a mouse, and a network interface (I/F) 25 connected to the network N. The CPU 20, the memory 21, the storage unit 22, the display 23, the input unit 24, and the network I/F 25 are connected to a bus 26.

The storage unit 22 is implemented by a hard disk drive (HDD), a solid state drive (SSD), a flash memory, or the like. A display control program 30 is stored in the storage unit 22 that serves as a storage medium. The CPU 20 reads out the display control program 30 from the storage unit 22, loads the display control program 30 into the memory 21, and executes the loaded display control program 30.

Figure 3:
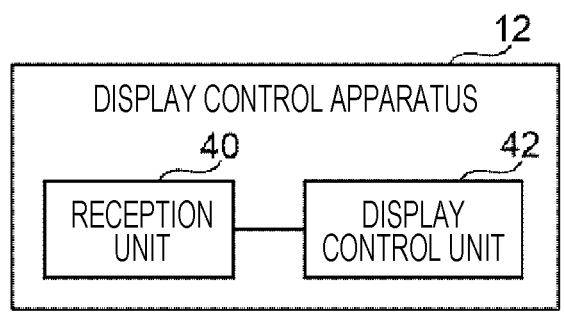
FIG. 3 is a block diagram illustrating an example of a functional configuration of the display control apparatus.

A functional configuration of the display control apparatus 12 according to the present embodiment will be described next with reference to FIG. 3. As illustrated in FIG. 3, the display control apparatus 12 includes a reception unit 40 and a display control unit 42. The CPU 20 executes the display control program 30 to function as the reception unit 40 and the display control unit 42.

The reception unit 40 receives various instructions input by a user via the input unit 24. Details of the various instructions given by the user will be described later.

Figure 4:
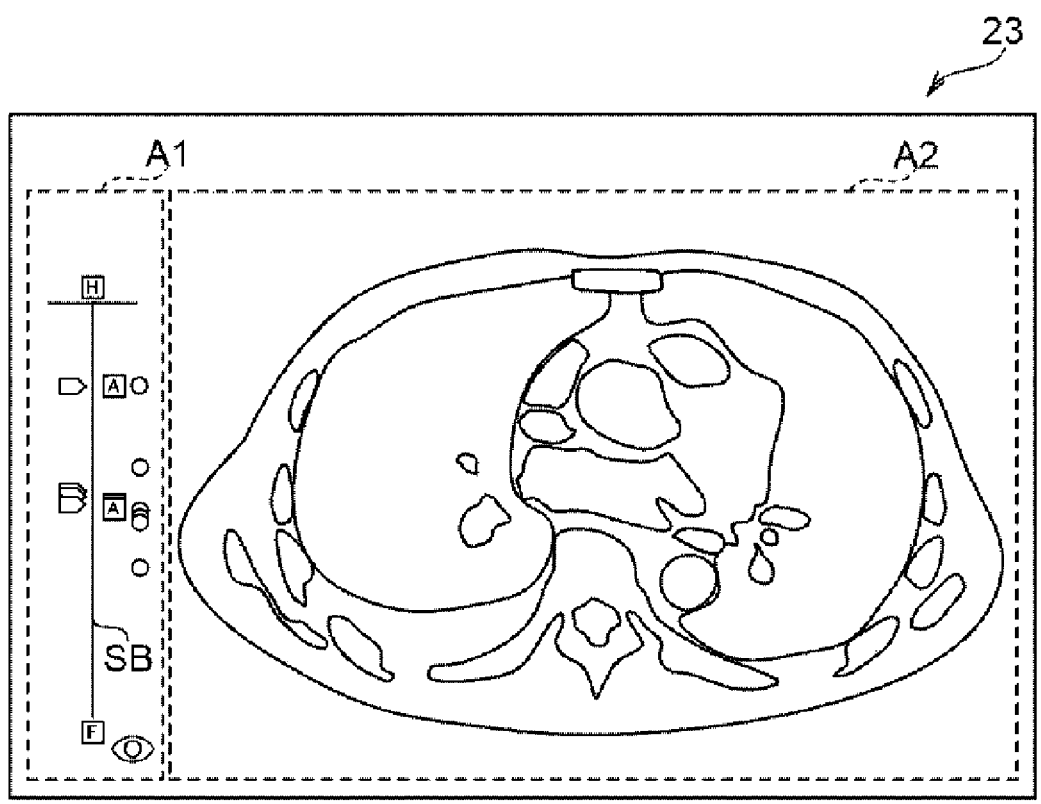
FIG. 4 is a diagram illustrating an example of a screen displaying a slider bar and a tomographic image.

As illustrated in FIG. 4, the display control unit 42 performs control to display, on the display 23, a slider bar SB for designating a tomographic position corresponding to each of a plurality of tomographic images for medical use obtained through imaging of a subject and a tomographic image corresponding to the designated tomographic position. These plurality of tomographic images for medical use obtained through imaging of the subject are a group of tomographic images constituting a three-dimensional medical image designated as a display target from among the three-dimensional medical images stored in the image storage apparatus 16. As illustrated in FIG. 4, the screen displayed on the display 23 includes a display region A1 in which the slider bar SB is displayed, and a display region A2 in which a tomographic image is displayed.

In the present embodiment, user-added additional information added by a user and computer-added additional information added by a computer are set to be added on a tomographic-image by tomographic-image basis. Hereinafter, when the user-added additional information and the computer-added additional information are collectively referred to without being distinguished from each other, they are referred to as "additional information". In the present embodiment, the additional information refers to additional information unique to each tomographic image such that additional information added to each tomographic image and a marking (described later) corresponding to the additional information are associated with each other on a one-to-one basis. Examples of the user-added additional information include a bookmark added as a mark for a tomographic image which the user desires to view later, and an annotation such as information on a region of interest (ROI) included in a tomographic image. Examples of the computer-added additional information include information on a region of interest detected through computer-aided diagnosis (CAD) or information on a region of interest detected through artificial intelligence (AI) image-based diagnosis. The region of interest used herein refers to a region to which the user pays attention, such as a region of a lesion such as a tumor. Examples of the information on a region of interest include an outline, a position, and an area of the region of interest. One or more computers may add the computer-added additional information. The computer that adds the computer-added additional information may be the display control apparatus 12, a control device included in the imaging apparatus 14, or the image storage apparatus 16. The computer that adds the computer-added additional information may be a computer such as an image processing apparatus external to the diagnosis assistance system 10.

Figure 5:
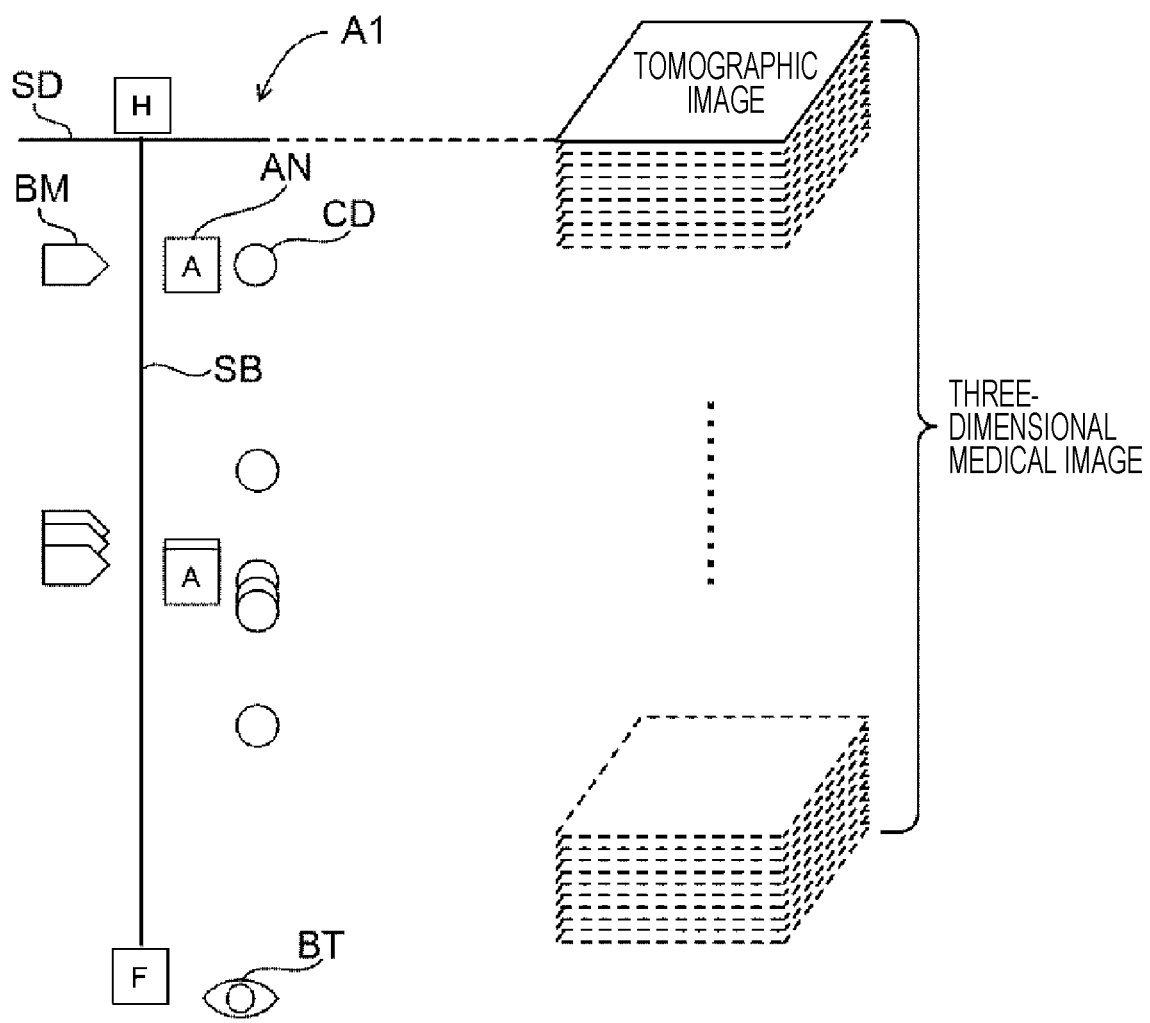
FIG. 5 is a diagram for describing the slider bar.

FIG. 5 illustrates only the display region A1 among the display regions A1 and A2 illustrated in FIG. 4. The display control unit 42 performs control to display a slider SD at a position corresponding to the designated tomographic position in a longitudinal direction of the slider bar SB. In FIG. 5, "H" surrounded by a rectangle represents a head side of the subject, and "F" surrounded by a rectangle represents a foot side. That is, the position of the slider SD on the slider bar SB indicates a tomographic position closer to the head side as the position of the slider SD approaches "H" and indicates a tomographic position closer to the foot side as the position of the slider SD approaches "F" among the tomographic positions of the respective tomographic images constituting the three-dimensional medical image. FIG. 5 illustrates an example in which a tomographic position closest to the head side is designated from among the tomographic positions of the respective tomographic images constituting the three-dimensional medical image. The slider bar SB and the slider SD are an example of a designation object for designating a tomographic position corresponding to each of a plurality of tomographic images in the present disclosure.

The display control unit 42 performs control to display, for a tomographic image with the additional information, a single marking that represents the additional information and enables a single tomographic image to be identified, at a position corresponding to the tomographic position of the tomographic image with the additional information on the slider bar SB.

Specifically, the display control unit 42 performs control to display, for a tomographic image with a bookmark, a marking BM representing the bookmark at a position corresponding to the tomographic position of the tomographic image with the bookmark on the slider bar SB. The display control unit 42 also performs control to display, for a tomographic image with an annotation, a marking AN representing the annotation at a position corresponding to the tomographic position of the tomographic image with the annotation on the slider bar SB. The display control unit 42 also performs control to display, for a tomographic image with computer-added additional information, a marking CD representing the computer-added additional information at a position corresponding to the tomographic position of the tomographic image with the computer-added additional information on the slider bar SB.

The display control unit 42 performs control to display the markings at the respective positions corresponding to the tomographic position on the slider bar SB such that the markings are shifted from each other in a direction orthogonal to a longitudinal direction of the slider bar SB (that is, in a longitudinal direction of the slider SD). Thus, even if a plurality of markings are present for the same tomographic position, the markings do not overlap.

The display control unit 42 also performs control to display a button BT for receiving a user input for switching between displaying and hiding of the computer-added additional information.

Via the input unit 24, the user designates a tomographic position of a tomographic image desired to be displayed. For example, the user drags the slider SD to the tomographic position, on the slider bar SB, of the tomographic image desired to be displayed to designate the tomographic position. For example, the user scrolls a mouse wheel to designate the tomographic position, on the slider bar SB, of the tomographic image desired to be displayed.

Figure 6:
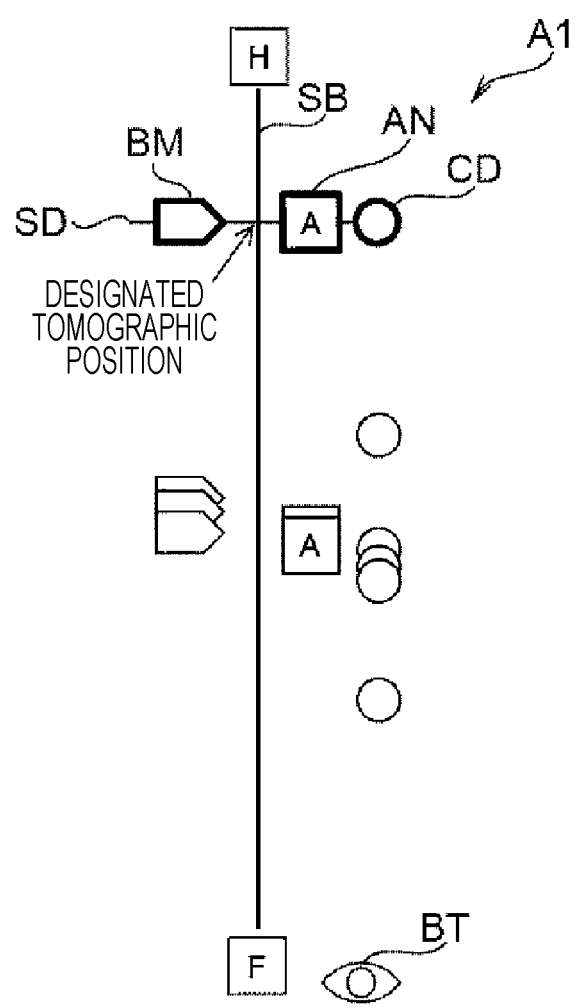
FIG. 6 is a diagram illustrating an example of a state in which markings representing additional information are emphasized.

When the additional information is added to the tomographic image corresponding to the designated tomographic position, the display control unit 42 performs control to display the marking representing the additional information in an emphasized manner. For example, as illustrated in FIG. 6, the display control unit 42 performs control for emphasized display by displaying outlines of the markings corresponding to the designated tomographic position to be thicker than outlines of markings corresponding to not-designated tomographic positions. FIG. 6 illustrates an example in which the bookmark, the annotation, and the computer-added additional information are added to the tomographic image corresponding to the designated tomographic position.

For example, the display control unit 42 may perform control for emphasized display by making a color of the outline of the marking corresponding to the designated tomographic position different from a color of the outlines of the markings corresponding to not-designated tomographic positions. For example, the display control unit 42 may perform control for emphasized display by displaying only the marking corresponding to the designated tomographic position to blink. These manners of emphasized display are merely illustrative, and manners other than these may be used.

Figure 7:
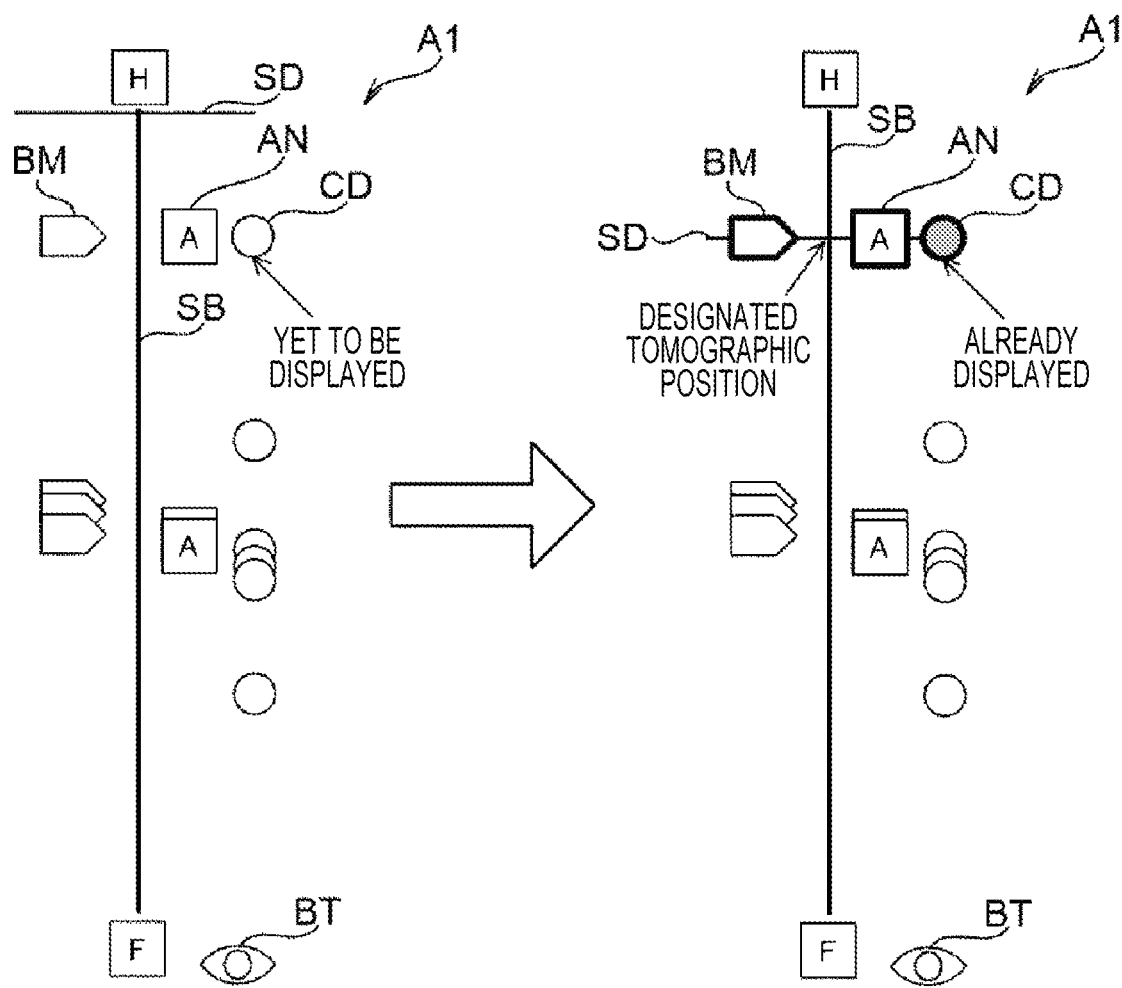
FIG. 7 is a diagram illustrating an example of markings representing already-displayed computer-added additional information and yet-to-be-displayed computer-added additional information.

As illustrated in FIG. 7, the display control unit 42 performs control to display the marking CD (illustrated as "YET TO BE DISPLAYED" on the left side in FIG. 7) representing the computer-added additional information added to a tomographic image yet to be displayed and the marking CD (illustrated as "ALREADY DISPLAYED" on the right side in FIG. 7) representing the computer-added additional information added to a tomographic image already displayed to be distinguishable from each other. Specifically, for example, when the background color is black, the display control unit 42 displays the marking CD representing the computer-added additional information added to the tomographic image yet to be displayed by filling the marking CD in a relatively bright color (for example, orange). On the other hand, when the tomographic position corresponding to that tomographic image is designated and the tomographic image is displayed to be a tomographic image already displayed, the display control unit 42 displays the marking CD added to the tomographic image already displayed by changing the color of the marking CD to a color closer to the background color (for example, a light gray). This allows the user to grasp, at a glance, whether or not the user has checked the computer-added additional information, that is, whether or not the user has checked the region of interest detected by the computer.

Figure 8:
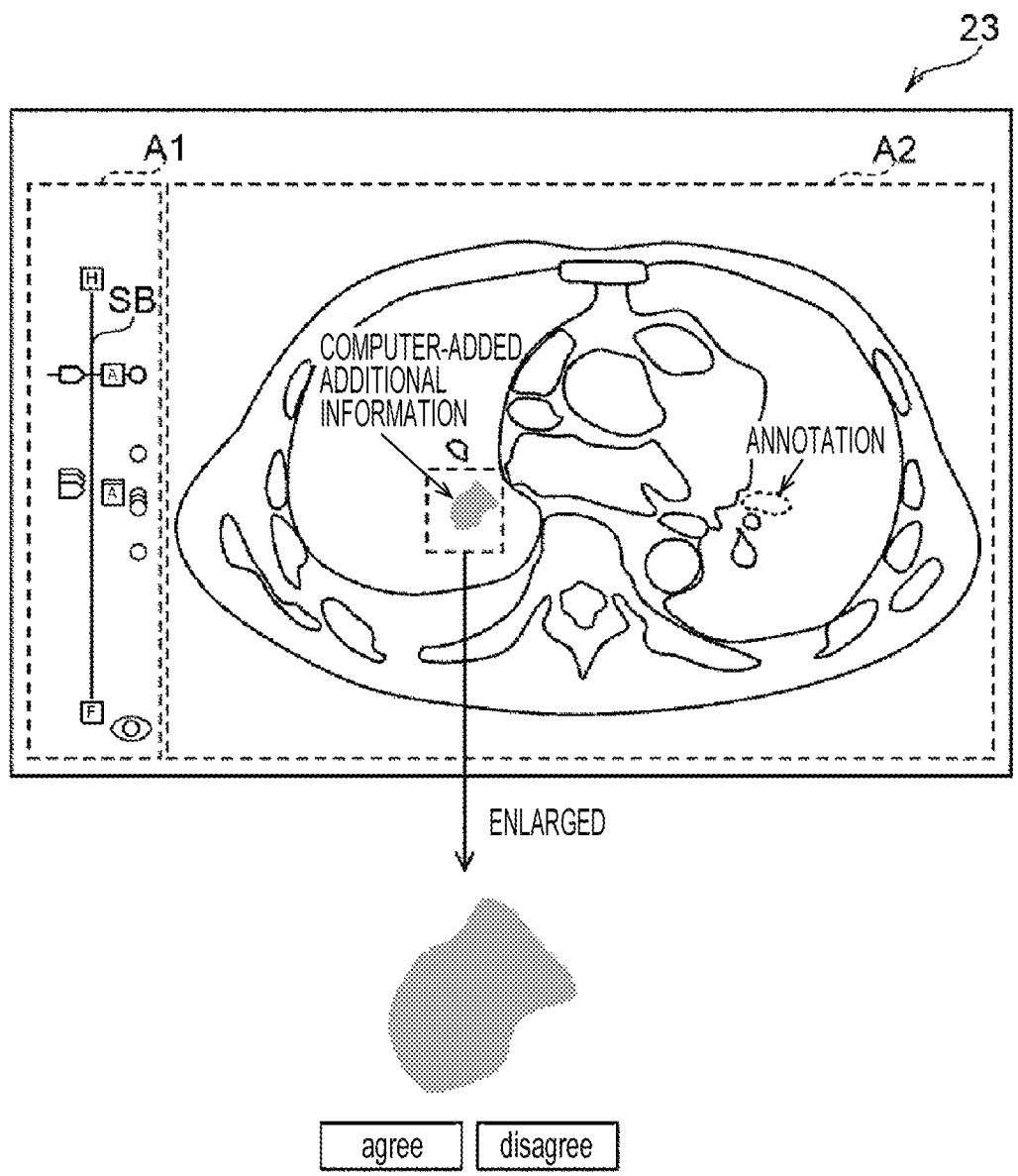
FIG. 8 is a diagram illustrating an example of computer-added additional information and an annotation which is one piece of user-added additional information displayed over a tomographic image.

As illustrated in FIG. 8, for a tomographic image with the computer-added additional information, the display control unit 42 performs control to display the computer-added additional information over the tomographic image. Specifically, for example, the display control unit 42 performs control to display a region of interest represented by the computer-added additional information in a state of being filled with a color (for example, orange) different from the color of the other region. The computer-added additional information is displayed without any outline in the initial state.

As illustrated in FIG. 8, for a tomographic image with the annotation, the display control unit 42 performs control to display the annotation over the tomographic image. Specifically, for example, the display control unit 42 performs control to display the outline of the region of interest represented by the annotation in a color (for example, white) different from the color of the region of interest represented by the computer-added additional information. Thus, the user can grasp whether the region of interest displayed in the tomographic image is detected through a user operation or by a computer. In FIG. 8, for ease of understanding, the outline of the region of interest represented by the annotation, which is a white solid outline, is illustrated as a broken line.

As illustrated in FIG. 8, when the computer-added additional information is displayed over the tomographic image, the display control unit 42 performs control to display a button (an "agree" button in the example of FIG. 8) to be designated by the user when the computer-added additional information is correct and a button (a "disagree" button in the example of FIG. 8) to be designated by the user when the computer-added additional information is incorrect. The case where the computer-added additional information is correct or incorrect more precisely refers to the case where the user determines the computer-added additional information to be correct or incorrect. When the outline of the region of interest represented by the computer-added additional information is correct, the user designates the "agree" button via the input unit 24. On the other hand, when the outline of the region of interest represented by the computer-added additional information is incorrect, the user designates the "disagree" button via the input unit 24.

Figure 9:
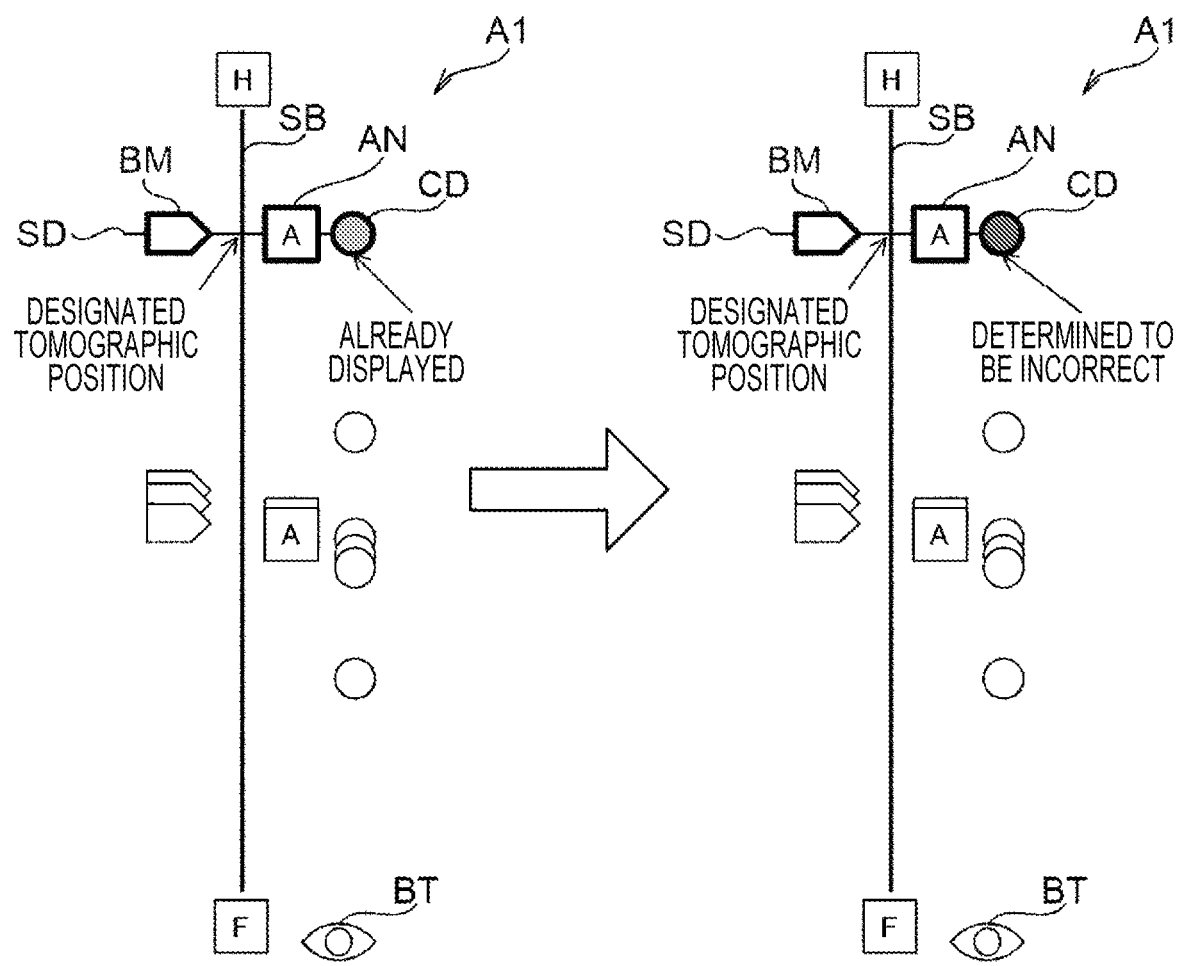
FIG. 9 is a diagram illustrating an example of a marking representing computer-added additional information determined to be incorrect.

In response to the reception unit 40 receiving an input indicating that the computer-added additional information is incorrect, that is, in response to the "disagree" button being designated, the display control unit 42 performs control below. In this case, the display control unit 42 performs control to change the color of the marking CD representing the computer-added additional information from the current display color to a color closer to the background color as illustrated in FIG. 9. Specifically, the display control unit 42 performs control to change the color of the marking CD from gray indicating that the corresponding tomographic image is already displayed to dark gray closer to black which is the background color. This can make the information that is added by the computer but is unnecessary for the user less conspicuous.

In response to the reception unit 40 receiving an input indicating that the computer-added additional information is correct, that is, in response to the "agree" button being designated, the display control unit 42 performs control below. In this case, the display control unit 42 performs control to add an annotation to the tomographic image with the computer-added additional information designated to be correct. Thus, the outline of the region of interest represented by the computer-added additional information designated to be correct is displayed, for example, in white as an annotation. In this case, since the computer-added additional information is still added, the user can grasp whether the region of interest is a region of interest that is not detected by the computer but is designated by the user himself/herself or a region of interest that is detected by the computer and is determined to be correct by the user himself/herself.

In detection by a computer, many regions of interest may be detected. Accordingly, before performing image-based diagnosis, the user may desire to hide the computer-added additional information. When the user desires to switch between displaying and hiding of the computer-added additional information, the user designates the button BT via the input unit 24.

Figure 10:
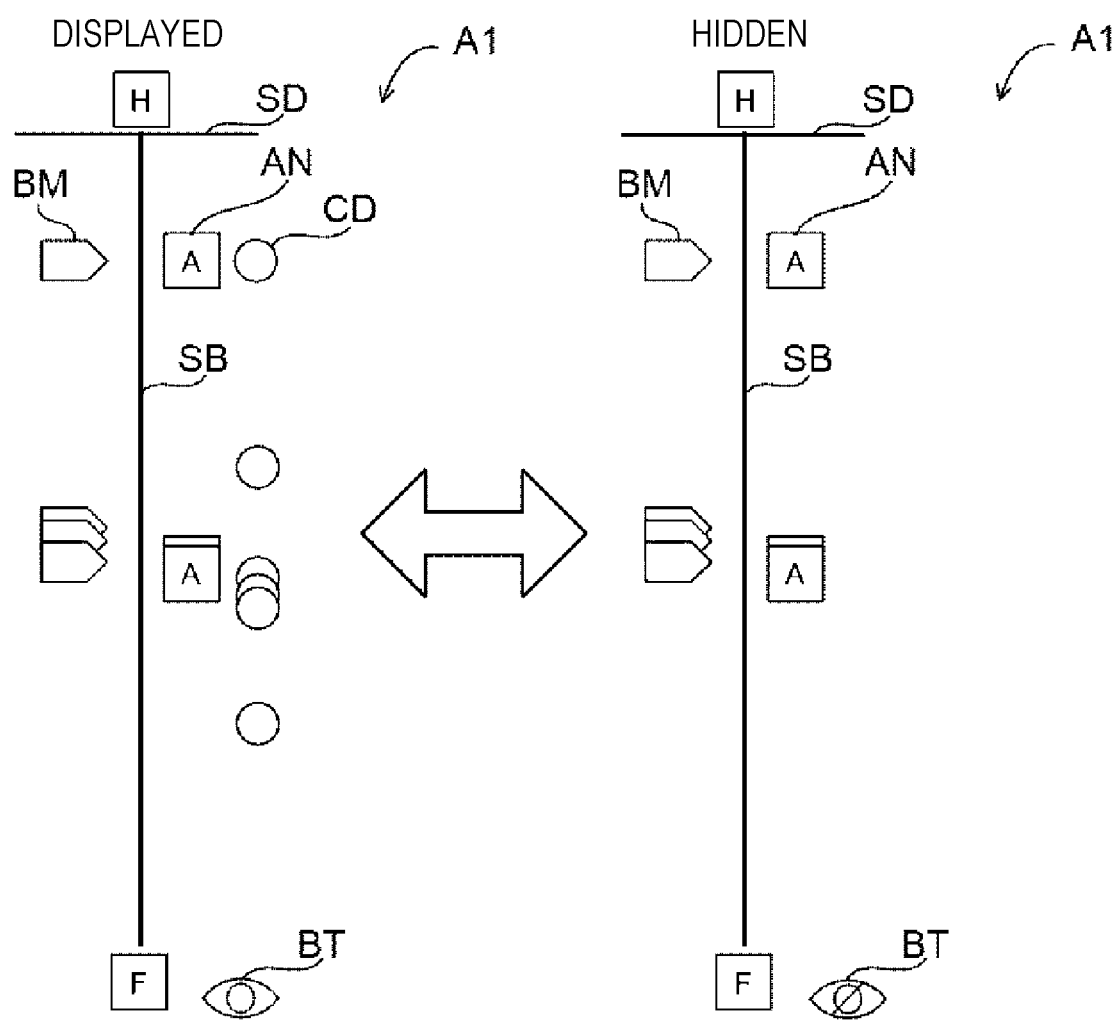
FIG. 10 is a diagram for describing switching between displaying and hiding of a marking representing the computer-added additional information.

In response to the reception unit 40 receiving an input for switching between displaying and hiding of the computer-added additional information, the display control unit 42 performs control to switch between displaying and hiding of the marking CD representing the computer-added additional information in accordance with the received input, as illustrated in FIG. 10. In the present embodiment, the display control unit 42 also performs control to switch between displaying and hiding of the computer-added additional information over the tomographic image in addition to the marking CD, as illustrated in FIG. 11.

Figure 12:
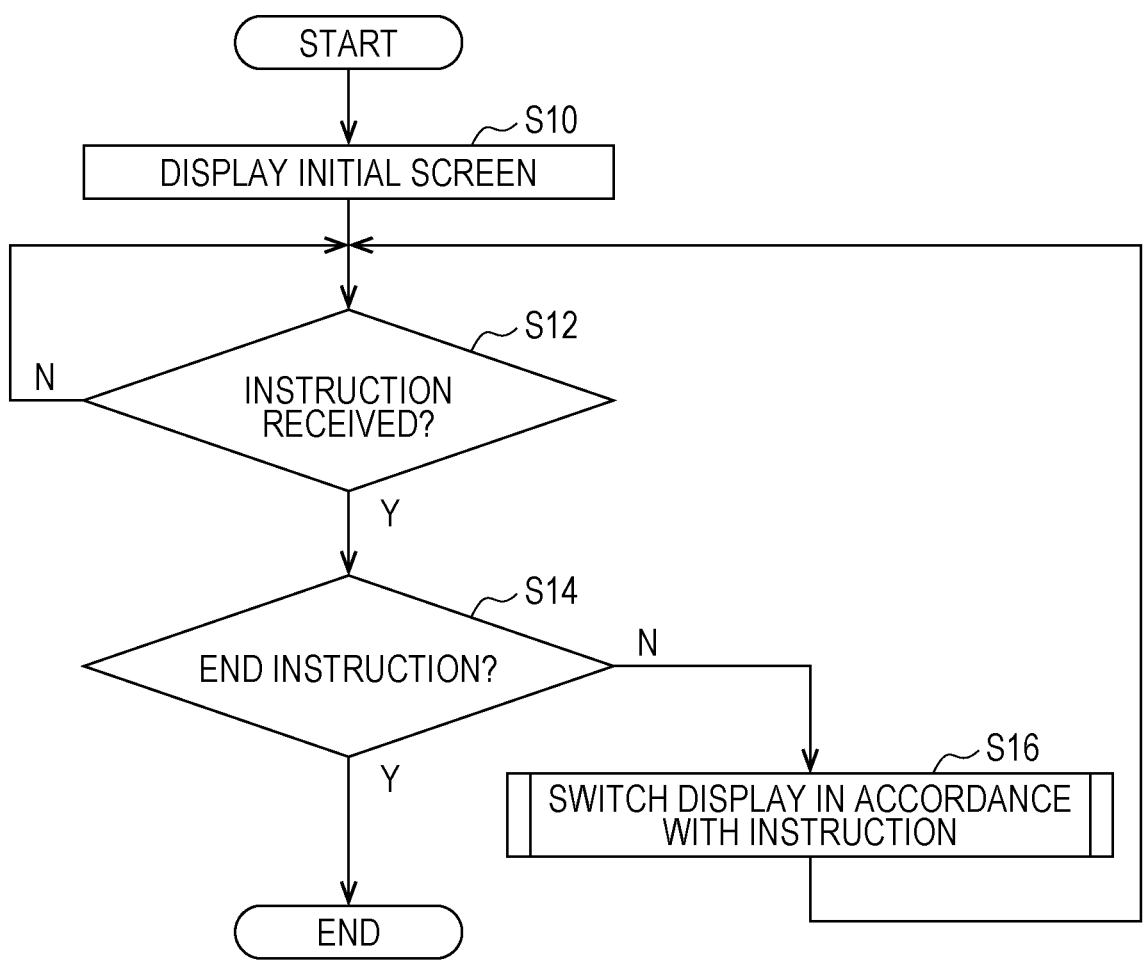
FIG. 12 is a flowchart illustrating an example of a display control process.

An operation of the display control apparatus 12 according to the present embodiment will be described next with reference to FIG. 12. The CPU 20 executes the display control program 30, so that a display control process illustrated in FIG. 12 is performed. The display control process is performed, for example, in response to the user inputting, via the input unit 24, an execution instruction and identification information that enables a group of tomographic images constituting a display-target three-dimensional medical image to be identified.

In step S10 in FIG. 12, the display control unit 42 acquires the group of tomographic images identified in accordance with the input identification information from the image storage apparatus 16, and performs control to display an initial screen on the display 23 based on the acquired group of tomographic images. Specifically, as described above, the display control unit 42 performs control to display, on the display 23, the slider bar SB for designating a tomographic position corresponding to each of the acquired tomographic images in the group and the tomographic image corresponding to the designated tomographic position. As described above, the display control unit 42 also performs control to display the slider SD at the position corresponding to the designated tomographic position in the longitudinal direction of the slider bar SB. An example will be described in which the tomographic position closest to the head side is used as the designated tomographic position in the initial screen. However, the designated tomographic position is not limited to this. In the initial screen, the tomographic position closest to the foot side or the tomographic position at the center may be used as the designated tomographic position.

As described above, the display control unit 42 performs control to display, for a tomographic image with the additional information among the tomographic images in the group, the marking representing the additional information at the position corresponding to the tomographic position of the tomographic image with the additional information on the slider bar SB. The display control unit 42 also performs control to display the button BT for receiving a user input for switching between displaying and hiding of the computer-added additional information. As a result of the processing of step S10, the screen illustrated in FIG. 4 is displayed on the display 23, for example. Note that when step S10 is performed for the second and subsequent times, the display control unit 42 sets the display state in which the most recent display state is inherited.

In step S12, the reception unit 40 waits until the reception unit 40 receives an instruction input by the user via the input unit 24. In response to the instruction being input by the user via the input unit 24, the determination in step S12 is positive and thus the process proceeds to step S14. In step S14, the reception unit 40 determines whether or not the instruction received in step S12 is an instruction to end the display. If this determination is negative, the process proceeds to step S16. In step S16, the display control unit 42 performs control to switch the display in accordance with the instruction received in step S12. In response to the end of the processing of step S16, the process returns to step S12. On the other hand, if the determination in step S14 is negative, the display control process ends. The display state of the display objects displayed in the respective display regions A1 and A2 at the time when this display control process ends is stored in the image storage apparatus 16 in association with the group of tomographic images, for example, so that the display state is inherited when step S10 is performed for the second and subsequent times.

Figure 13:
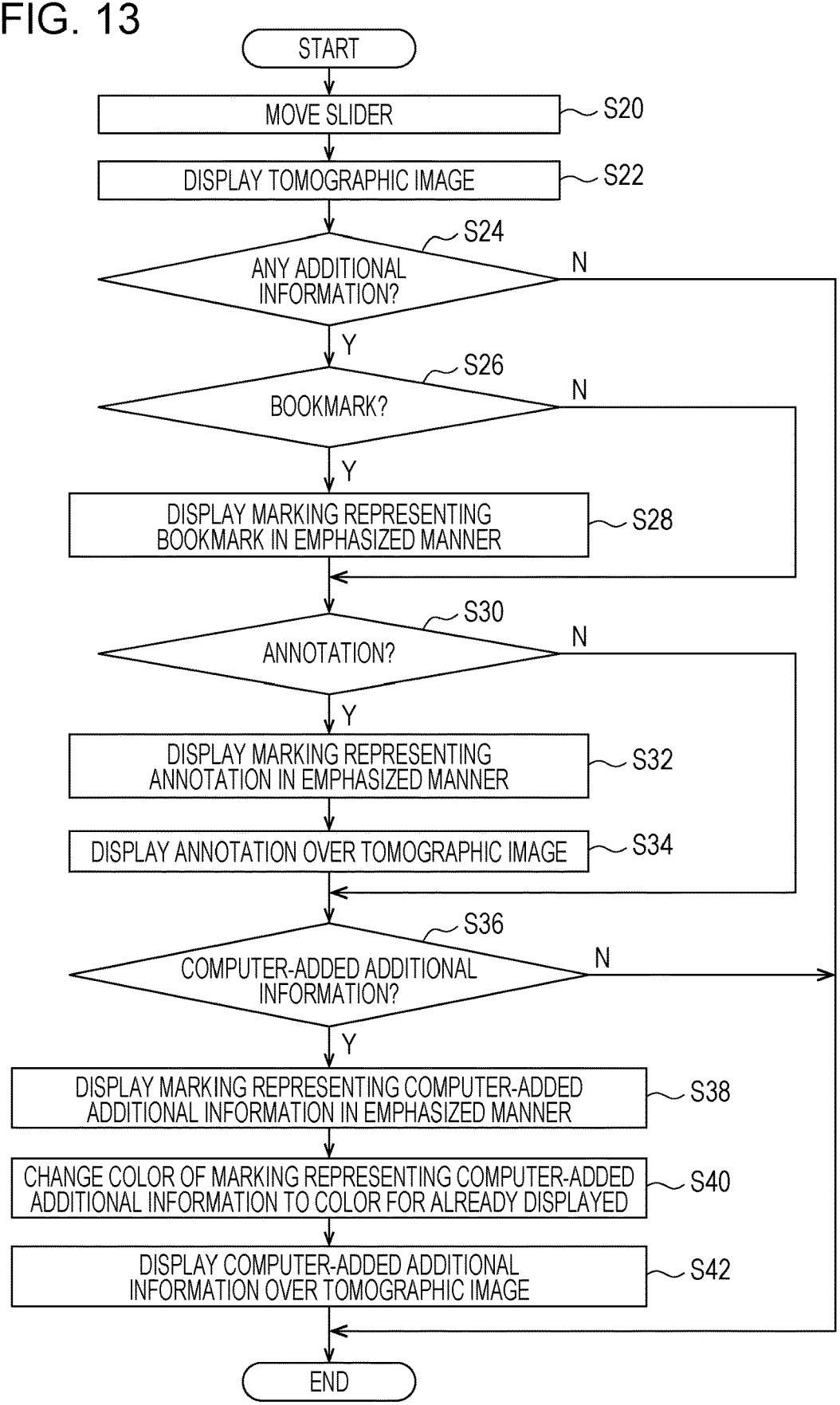
FIG. 13 is a flowchart illustrating an example of a processing routine in the case where a tomographic position is designated.

If the instruction received in step S12 is an instruction to designate a tomographic position through a drag operation on the slider SD, a scroll operation on a mouse wheel, or the like, a processing routine illustrated in FIG. 13 is performed in step S16.

In step S20 in FIG. 13, the display control unit 42 performs control to move the slider SD to the position, on the slider bar SB, corresponding to the tomographic position designated through the user operation. In step S22, the display control unit 42 performs control to switch the tomographic image in the display region A2 to the tomographic image at the designated tomographic position.

In step S24, the display control unit 42 determines whether or not the additional information is added to the tomographic image at the designated tomographic position. If this determination is positive, the process proceeds to step S26. In step S26, the display control unit 42 determines whether or not the bookmark is added to the tomographic image at the designated tomographic position. If this determination is positive, the process proceeds to step S28.

In step S28, the display control unit 42 performs control to display the marking BM representing the bookmark added to the tomographic image at the designated tomographic position in an emphasized manner. If the determination in step S26 is negative, the processing of step S28 is not performed and the process proceeds to step S30.

In step S30, the display control unit 42 determines whether or not the annotation is added to the tomographic image at the designated tomographic position. If this determination is positive, the process proceeds to step S32. In step S32, the display control unit 42 performs control to display the marking AN representing the annotation added to the tomographic image at the designated tomographic position in an emphasized manner. In step S34, the display control unit 42 performs control to display the annotation over the tomographic image as described above. If the determination in step S30 is negative, the processing from S32 to step S34 is not performed and the process proceeds to step S36.

In step S36, the display control unit 42 determines whether or not the computer-added additional information is added to the tomographic image at the designated tomographic position. If this determination is positive, the process proceeds to step S38. In step S38, the display control unit 42 performs control to display the marking CD representing the computer-added additional information added to the tomographic image at the designated tomographic position in an emphasized manner. In step S40, the display control unit 42 changes the color of the marking CD representing the computer-added additional information added to the tomographic image at the designated tomographic position to a color indicating that the tomographic image is already displayed as described above. If the color of this marking CD is the color indicating that the corresponding tomographic image is already displayed or the color indicating that the computer-added additional information is incorrect, the display control unit 42 does not change the color of the marking CD. In step S42, the display control unit 42 performs control to display the computer-added additional information over the tomographic image as described above.

In response to the end of the processing of step S42, the processing routine illustrated in FIG. 13 ends. If the determination in step S36 is negative, the processing from S38 to step S42 is not performed and the processing routine illustrated in FIG. 13 ends. If the determination in step S24 is negative, the processing from S26 to step S42 is not performed and the processing routine illustrated in FIG. 13 ends.

Figure 14:
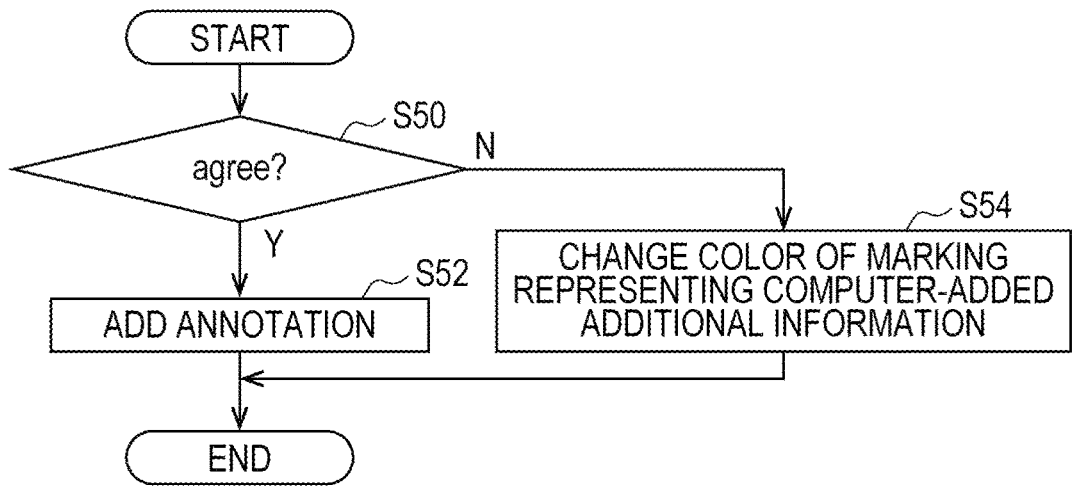
FIG. 14 is a flowchart illustrating an example of a processing routine in the case where a determination is made on the computer-added additional information by the user.

If the instruction received in step S12 is an instruction indicating whether the computer-added additional information is correct or incorrect resulting from designation of the "agree" button or the "disagree" button, a processing routine illustrated in FIG. 14 is performed in step S16.

In step S50 in FIG. 14, the reception unit 40 determines whether or not the received instruction is an input indicating that the computer-added additional information is correct, that is, whether or not the "agree" button is designated. If this determination is positive, the process proceeds to step S52. If the instruction received by the reception unit 40 is an input indicating that the computer-added additional information is incorrect, that is, the "disagree" button is designated, the determination in step S50 is negative and thus the process proceeds to step SM.

In step S52, the display control unit 42 performs control to add the annotation to the tomographic image with the computer-added additional information designated to be correct as described above. In response to the end of the processing of step S52, the processing routine illustrated in FIG. 14 ends. In step S54, the display control unit 42 performs control to change the color of the marking CD representing the computer-added additional information from the current display color to a color closer to the background color as described above. In response to the end of the processing of step S54, the processing routine illustrated in FIG. 14 ends.

Figure 15:
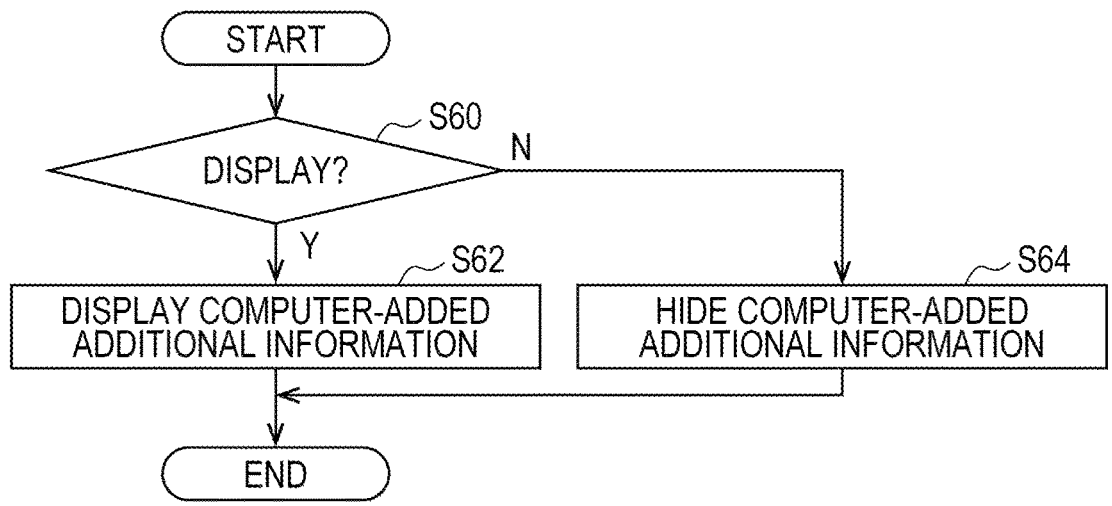
FIG. 15 is a flowchart illustrating an example of a processing routine for switching between displaying and hiding of the computer-added additional information.

If the instruction received in step S12 is an instruction to switch between displaying and hiding of the computer-added additional information as a result of designation of the button BT, a processing routine illustrated in FIG. 15 is performed in step S16.

In step S60 in FIG. 15, the reception unit 40 determines whether or not the received instruction is an instruction to display the computer-added additional information. If this determination is positive, the process proceeds to step S62. If the instruction received by the reception unit 40 is an instruction to hide the computer-added additional information, the determination in step S60 is negative and thus the process proceeds to step S64.

In step S62, the display control unit 42 performs control to display the marking CD representing the computer-added additional information and display the computer-added additional information over the tomographic image as described above. In response to the end of the processing of step S62, the processing routine illustrated in FIG. 15 ends. In step S64, the display control unit 42 performs control to hide the marking CD representing the computer-added additional information and hide the computer-added additional information over the tomographic image as described above. In response to the end of the processing of step S64, the processing routine illustrated in FIG. 15 ends.

As described above, according to the present embodiment, unique additional information can be added on a tomographic-image by tomographic-image basis, and a single marking enables a single tomographic image to be identified. When the additional information is added to the tomographic image corresponding to the designated tomographic position, the marking representing the additional information is displayed in an emphasized manner. Thus, it is easier for the user to grasp whether or not the unique additional information is added to the tomographic image corresponding to the tomographic position designated on the slider bar SB.

Figure 16:
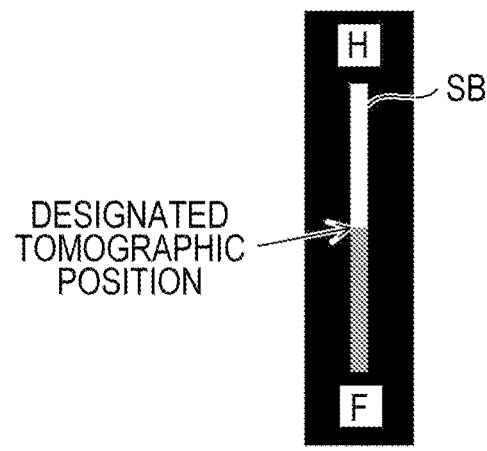
FIG. 16 is a diagram illustrating an example of a slider bar according to a modification.

In the embodiment described above, the display control unit 42 may perform control to, without displaying the slider SD, display the slider bar SB such that a color of a portion from one end of the slider bar SB to the designated tomographic position and a color of a portion from the other end of the slider bar SB to the designated tomographic position are different from each other, as illustrated in FIG. 16. In this case, the slider SD which is an object exclusively used for designating the tomographic position need not be displayed. Alternatively, in this case, the slider SD may be displayed as in the embodiment above.

Figure 17:
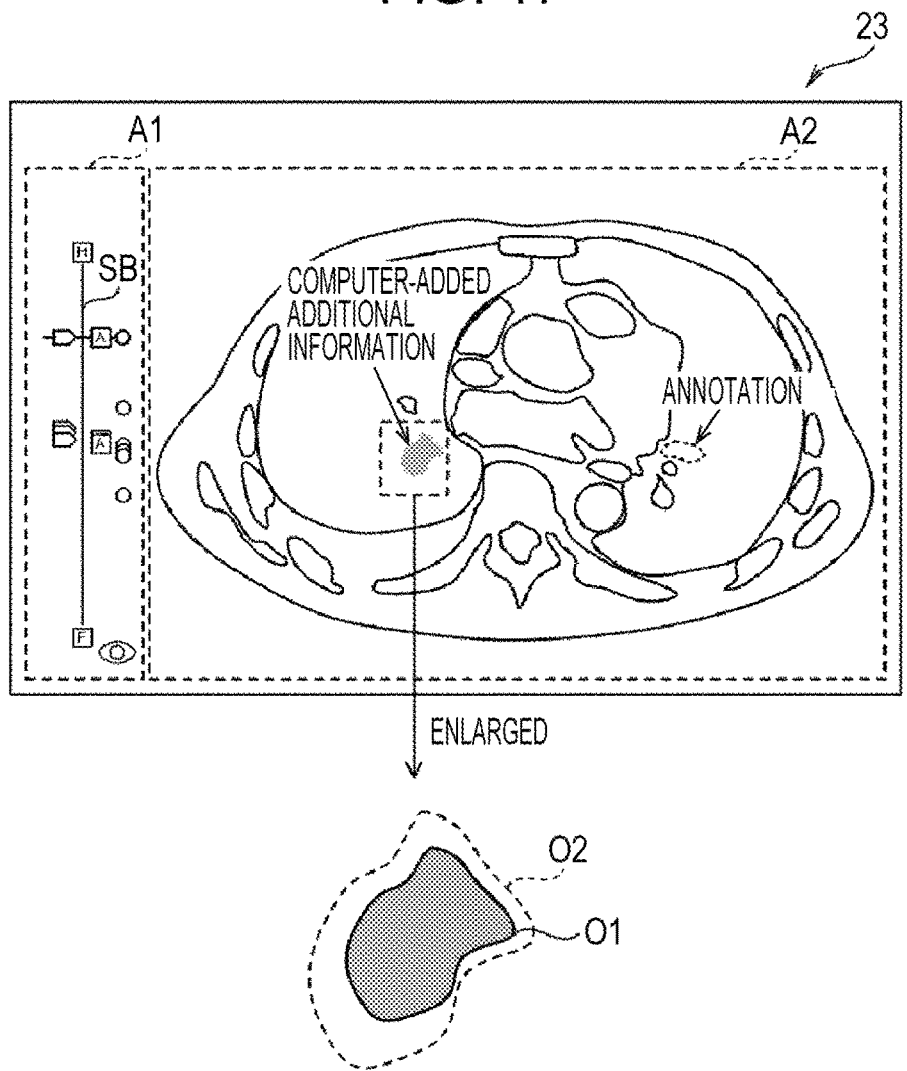
FIG. 17 is a diagram illustrating an example of a display state of computer-added additional information according to a modification.

In the embodiment described above, for a tomographic image with the computer-added additional information, the display control unit 42 may perform control to further display, in addition to an outline O1 of a region of interest represented by the computer-added additional information added to the tomographic image, an outline O2 of the region of interest as illustrated in FIG. 17. In this case, for example, the display control unit 42 performs control to display, as the outline O2, an outline of the region of interest represented by the computer-added additional information added to any of the other tomographic images in which the same region of interest is detected. Specifically, the display control unit 42 performs control to display, as the outline O2, the largest outline among outlines of the region of interest represented by the computer-added additional information added to some of the other tomographic images in which the same region of interest is detected. Examples of the largest outline used herein include an outline for the largest area and an outline with the longest length.

Figure 18:
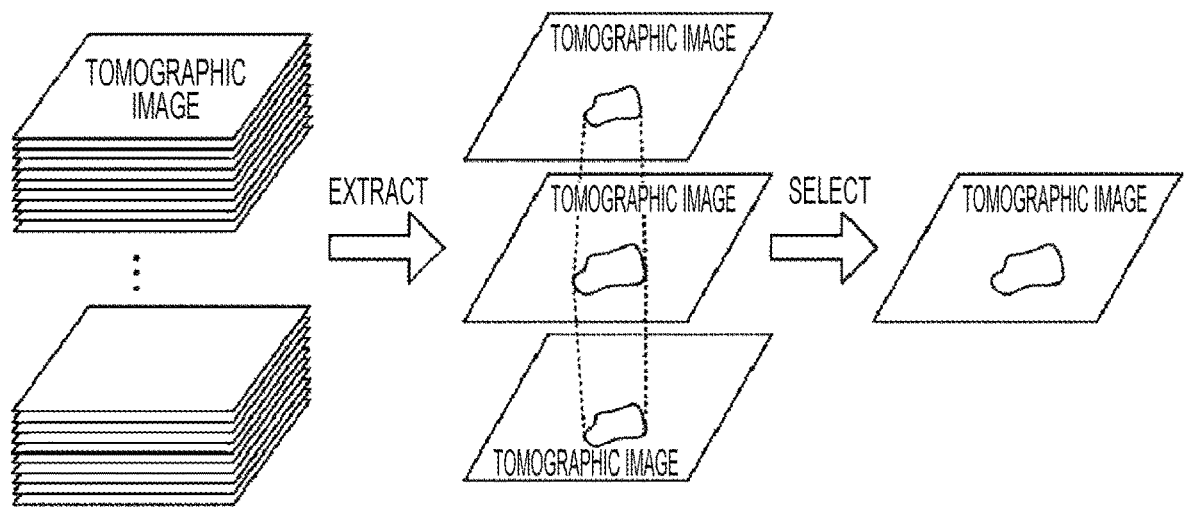
FIG. 18 is a diagram for describing a process of adding computer-added additional information according to a modification.

In the embodiment described above, the case has been described where the computer adds the computer-added additional information to all the tomographic images in which the region of interest is detected. However, the configuration is not limited to this. As illustrated in FIG. 18, the computer may extract a group of tomographic images containing the same target (region of interest, for example) from a plurality of tomographic images constituting a three-dimensional medical image, select a representative tomographic image from the extracted group of tomographic images, and add the computer-added additional information only to the selected tomographic image. In this case, for example, the computer identifies, as the same region of interest, regions of interest for which an absolute value of a difference between barycentric positions of the regions of interest detected in consecutive tomographic images is less than or equal to a predetermined first threshold value and an absolute value of a difference between areas of the regions of interest is less than or equal to a predetermined second threshold value. In this case, values set in advance as upper-limit values of the respective differences of the same region of interest between consecutive tomographic images can be used as the first threshold value and the second threshold value. In this case, for example, the computer extracts, as the representative tomographic image, a tomographic image in which a region of interest having the largest area or the longest outline length is detected from the extracted group of tomographic images. The computer in this case may be the display control apparatus 12, a control device included in the imaging apparatus 14, the image storage apparatus 16, or a computer external to the diagnosis assistance system 10.

The processing performed by the computer to select the tomographic image to which the additional information is to be added in this case may be performed in the same manner by the user via the input unit 24. The user-added additional information in this case is information added by the user to the representative tomographic image of the group of tomographic images containing the same target among the plurality of tomographic images.

Figure 19:
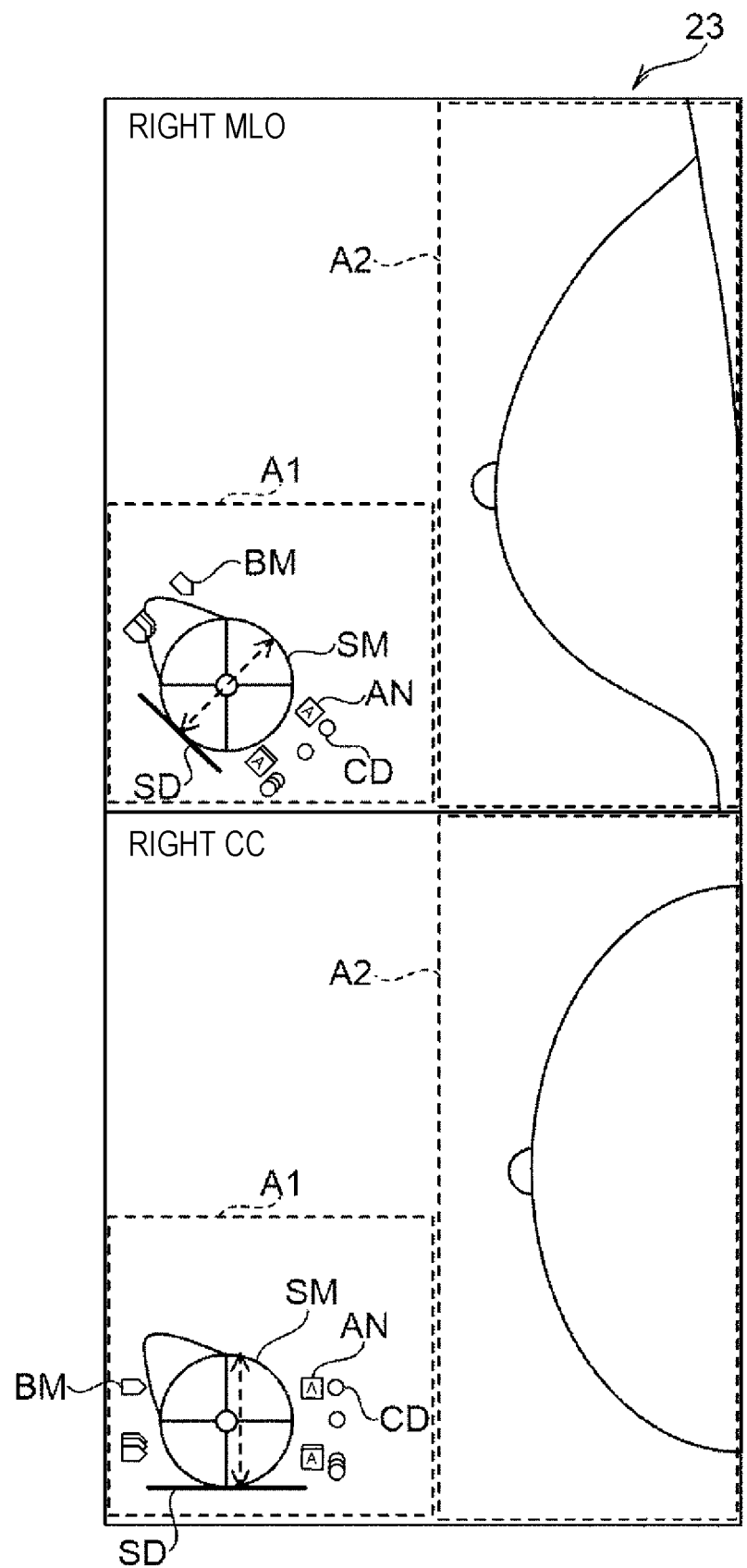
FIG. 19 is a diagram illustrating an example of a screen displaying a schema and a tomographic image according to a modification.

In the embodiment described above, the case has been described where the slider bar SB and the slider SD are used as a designation object for designating a tomographic position corresponding to each of a plurality of tomographic images. However, the designation object is not limited to this. For example, as illustrated in FIG. 19, a schema SM and the slider SD may be used as the designation object for designating a tomographic position corresponding to each of a plurality of tomographic images. The schema SM used herein refers to a schematic diagram schematically illustrating a part of a human body. FIG. 19 illustrates an example in which a plurality of tomographic images for medical use obtained through tomosynthesis imaging using a mammography apparatus are used as the plurality of tomographic images. The upper part of FIG. 19 illustrates a tomographic image obtained by performing medio-lateral oblique (MLO) imaging on the right breast, and the lower part of FIG. 19 illustrates a tomographic image obtained by performing cranio-caudal (CC) imaging on the right breast. In FIG. 19, the depth direction of the tomographic images, that is, the moving direction of the slider SD is indicated by a double-headed dash arrow. For example, the user drags the slider SD to the tomographic position, on the schema SM, of the tomographic image which the user desires to display to designate the tomographic position also in this configuration example. In this case, when the additional information is added to the tomographic image corresponding to the designated tomographic position, the marking indicating the additional information is displayed in an emphasized manner. In this configuration example, the markings AN and CD may be displayed in the schema SM so that the two-dimensional arrangement when the breast is viewed from the front can be understood.

Both the slider SD and the slider bar SB illustrated in FIGS. 4 and 5 and the schema SM and the slider SD illustrated in FIG. 19 may be displayed in the display region A1. In this configuration example, an operation performed on either one of these may be reflected in the other.

In the embodiment described above, for example, various processors mentioned below can be used as a hardware structure of processing units such as the reception unit 40 and the display control unit 42 that perform various processes. The aforementioned various processors include, in addition to a CPU which is a general-purpose processor that executes software (program) to function as the various processing units as described above, a programmable logic device (PLD), such as a field programmable gate array (FPGA), which is a processor whose circuitry is changeable after production; a dedicated electric circuit, such as an application specific integrated circuit (ASIC), which is a processor having circuitry designed exclusively for executing specific processing; and the like.

A single processing unit may be constituted by one of these various processors, or by a combination of two or more processors of the same kind or different kinds (for example, a combination of a plurality of FPGAs or a combination of a CPU and an FPGA). In addition, a plurality of processing units may be constituted by a single processor.

Examples in which the plurality of processing units are constituted by a single processor include a first configuration, as exemplified by computers such as a server and a client, in which a combination of one or more CPUs and software constitutes the single processor and this processor functions as the plurality of processing units. The examples also include a second configuration, as exemplified by a System On Chip (SoC) or the like, in which the processor that implements functions of the entire system including the plurality of processing units on a single integrated circuit (IC) chip is used. As described above, the various processing units are constituted using one or more of the various processors above in terms of the hardware structure.

More specifically, electric circuitry in which circuit elements such as semiconductor elements are combined can be used in terms of the hardware structure of these various processors.

In the embodiment above, the configuration has been described in which the display control program 30 is stored (installed) in the storage unit 22 in advance. However, the configuration is not limited to this. The display control program 30 may be provided in a form of a recording medium, such as a compact disc read-only memory (CD-ROM), a digital versatile disc read-only memory (DVD-ROM), or a Universal Serial Bus (USB) memory, on which the display control program 30 is recorded. The display control program 30 may also be downloaded from an external apparatus via a network.

The disclosure of JP2020-040359 filed Mar. 9, 2020 is incorporated herein by reference in its entirety. All the documents, patent applications, and technical standards mentioned in this specification are incorporated herein by reference to the same extent as if the individual documents, patent applications, and technical standards were specifically and individually described to be incorporated by reference.

What is claimed is:

1. A display control apparatus coupled to a display, comprising:
   at least one processor, the processor being configured to display, on the display:
   a designation object for designating a tomographic position corresponding to each of a plurality of tomographic images for medical use obtained through imaging of a subject;
   a tomographic image corresponding to the tomographic position designated by the designation object;
   an additional information displayed together with the tomographic image, the additional information including at least one of user-added additional information added by a user or computer-added additional information added by a computer, the additional information being unique to each of the plurality of tomographic images, and being added to the tomographic image by tomographic-image basis; and
   a plurality of markings displayed on the designation object at a position corresponding to a tomographic position of the tomographic image including the additional information in a depth direction of the designation object, each marking representing the tomographic image being added with the additional information and being configured to identify a single tomographic image by a single marking,
   wherein the processor is configured to display the corresponding marking on the designation object in an emphasized manner, in a case where the tomographic image corresponding to the designated tomographic position and being presently displayed, is added with the additional information.

2. The display control apparatus according to claim 1, wherein the designation object includes a slider bar.

3. The display control apparatus according to claim 1, wherein the designation object includes a schema.

4. The display control apparatus according to claim 2, wherein the processor performs control to display the slider bar such that a color of a portion from an end of the slider bar to the designated tomographic position and a color of a portion from an other end of the slider bar to the designated tomographic position are different from each other.

5. The display control apparatus according to claim 1, wherein
the additional information includes the computer-added additional information, and
the processor performs control to display the marking representing the computer-added additional information added to a yet-to-be-displayed tomographic image and the marking representing the computer-added additional information added to an already-displayed tomographic image to be distinguishable from each other.

6. The display control apparatus according to claim 1, wherein
the additional information includes the computer-added additional information, and
the processor
receives an input indicating whether or not the computer-added additional information is correct, and
performs control to change a color of the marking representing the computer-added additional information from a current display color to a color closer to a background color in a case of receiving an input indicating that the computer-added additional information is incorrect.

7. The display control apparatus according to claim 1, wherein
the additional information includes the computer-added additional information, and
the processor
receives an input for switching between displaying and hiding of the computer-added additional information, and
performs control to switch between displaying and hiding of the marking representing the computer-added additional information in accordance with the received input.

8. The display control apparatus according to claim 7, wherein the processor
performs control to display, for a tomographic image with the computer-added additional information, the computer-added additional information over the tomographic image, and
performs control to switch between displaying and hiding of both the marking representing the computer-added additional information and the computer-added additional information over the tomographic image in accordance with the received input.

9. The display control apparatus according to claim 1, wherein
the additional information includes, as the computer-added additional information, an outline of a region of interest in the tomographic image, and
the processor
performs control to display, in a case where the outline of the region of interest is added to the tomographic image corresponding to the designated tomographic position, the outline of the region of interest over the tomographic image, and
performs control to further display an outline of the region of interest added to any of other tomographic images in which a region of interest identical to the region of interest being displayed is detected.

10. The display control apparatus according to claim 9, wherein the processor performs control to display a largest outline among outlines of the region of interest added to the other tomographic images.

11. The display control apparatus according to claim 1, wherein
the computer
extracts a group of tomographic images containing an identical target from the plurality of tomographic images, and
selects a representative tomographic image from the extracted group of tomographic images, and
the computer-added additional information includes information to be added to the selected tomographic image.

12. The display control apparatus according to claim 1, wherein the user-added additional information includes information added by the user to a representative tomographic image of a group of tomographic images containing an identical target among the plurality of tomographic images.

13. A display control method performed by a processor included in a display control apparatus coupled to a display, the display control method comprising:
displaying, on the display:
a designation object for designating a tomographic position corresponding to each of a plurality of tomographic images for medical use obtained through imaging of a subject;
a tomographic image corresponding to the tomographic position designated by the designation object;
an additional information displayed together with the tomographic image, the additional information including at least one of user-added additional information added by a user or computer-added additional information added by a computer, the additional information being unique to each of the plurality of tomographic images, and being added to the tomographic image by tomographic-image basis; and
a plurality of markings displayed on the designation object at a position corresponding to a tomographic position of the tomographic image including the additional information in a depth direction of the designation object, each marking representing the tomographic image being added with the additional information and being configured to identify a single tomographic image by a single marking,
wherein, the corresponding marking on the designation object is displayed in an emphasized manner, in a case where the tomographic image corresponding to the designated tomographic position and being presently displayed, is added with the additional information.

14. A non-transitory computer-readable storage medium storing a display control program for causing a processor included in a display control apparatus coupled to a display, to perform a process, the process comprising:
displaying, on the display:
a designation object for designating a tomographic position corresponding to each of a plurality of tomographic images for medical use obtained through imaging of a subject;
a tomographic image corresponding to the tomographic position designated by the designation object;
an additional information displayed together with the tomographic image, the additional information including at least one of user-added additional information added by a user or computer-added additional information added by a computer the additional information being unique to each of the plurality of tomographic images, and being added to the tomographic image by tomographic-image basis; and a plurality of markings displayed on the designation object at a position corresponding to a tomographic position of the tomographic image including the additional information in a depth direction of the designation object, each marking representing the tomographic image being added with the additional information and being configured to identify a single tomographic image by a single marking, wherein, the corresponding marking on the designation object is displayed in an emphasized manner, in a case where the tomographic image corresponding to the designated tomographic position and being presently displayed, is added with the additional information.

* * * * *